(12) United States Patent
Rode et al.

(10) Patent No.: US 6,437,582 B1
(45) Date of Patent: Aug. 20, 2002

(54) DEVICE FOR THE MEASUREMENT OF MOISTURE OF HARVESTED CROP

(75) Inventors: Hans-Jürgen Rode, Harrislee; Arnold Rutz, Zweibrücken, both of (DE)

(73) Assignee: Deere & Company, Moline, IL (US)

( * ) Notice: Subject to any disclaimer, the term of this patent is extended or adjusted under 35 U.S.C. 154(b) by 0 days.

(21) Appl. No.: 09/618,847

(22) Filed: Jul. 18, 2000

(30) Foreign Application Priority Data

Jul. 24, 1999 (DE) .......................................... 199 34 881

(51) Int. Cl.[7] .............................................. G01R 27/26
(52) U.S. Cl. ..................... 324/664; 324/658; 73/335.04
(58) Field of Search ................................ 324/637, 640, 324/664, 668, 658, 689, 96; 222/63; 73/29.1, 335.04, 861.73, 861, 193, 1.2 A, 1.2 C, 1.2 R

(56) References Cited

U.S. PATENT DOCUMENTS

| | | | |
|---|---|---|---|
| 1,822,604 A | | 9/1931 | Simmons et al. |
| 3,693,079 A | * | 9/1972 | Walker ........................ 324/640 |
| 4,361,801 A | * | 11/1982 | Meyer ........................ 324/638 |
| 4,484,133 A | * | 11/1984 | Riggin ........................ 324/637 |
| 4,584,522 A | | 4/1986 | Varela ....................... 324/61 R |
| 4,896,795 A | * | 1/1990 | Ediger ........................... 222/63 |
| 5,218,309 A | | 6/1993 | Nelson et al. ............... 324/664 |
| 5,859,536 A | * | 1/1999 | Paul Stockton ............. 324/664 |
| 6,285,198 B1 | * | 9/2001 | Nelson ........................ 324/664 |

FOREIGN PATENT DOCUMENTS

| | | |
|---|---|---|
| CA | 2 182 989 A | 3/1997 |
| DE | 1 300 316 | 7/1969 |
| EP | 0 389 320 A | 9/1990 |
| GB | 396 098 A | 7/1933 |

* cited by examiner

Primary Examiner—Michael Sherry
Assistant Examiner—Trung Nguyen

(57) ABSTRACT

A device for the measurement of the moisture of harvested crop including a measurement capacitor (52) with two spaced electrodes (78, 80, 82), between which harvested crop can be introduced. The capacitor (52) is connected to an inductance (104) of a resonance circuit (106). For improved precision, it is proposed that the resonance circuit (106) be supplied with a measurement signal in the form of an alternating voltage with variable frequency and that a parameter of the resonance circuit (106), preferably resonant frequency dependent upon the capacitance of the capacitor (52), be detected at various frequencies and used for the determination of the moisture.

21 Claims, 4 Drawing Sheets

DEVICE FOR THE MEASUREMENT OF MOISTURE OF HARVESTED CROP

FIELD OF THE INVENTION

The invention relates to a device for the measurement of the moisture of harvested crop, the device including a measurement capacitor equipped with two electrodes between which crop can be positioned and connected to an inductor to define a resonance circuit, and a process for the measurement of the moisture of a harvested crop.

RELATED ART

An arrangement that operates on a capacitive measurement principle for the measurement of moisture of harvested crop is shown in U.S. Pat. No. 4,584,522. A container is filled with harvested crop of unknown moisture, and the moisture of the crop can be determined on the basis of the change in the capacitance of an electrode in the form of a capacitor plate with respect to a second electrode. A dry crop has a relatively low relative permittivity and produces only a small change in capacitance compared to an empty container, whereas a wet crop with high relative permittivity produces a larger change in capacitance. For this measurement the capacitor with unknown capacitance C is charged with a predetermined voltage and is discharged by cutting off the source of the charge over a resistance R, where the voltage applied after a certain time applied to RC module is a measure of the capacitance C.

DE 1300316 B describes an arrangement for the continuous measurement of bulk material in which the dielectric losses of the measurement capacitor are used as a measure of the water content of the material to be measured. Hence a parasitic (Ohmic) resistance of the capacitor charged with high frequency alternating current is measured.

Furthermore resonance measurement circuits have been proposed for measurement devices for the determination of moisture. In the measurement arrangements of this class described by W. Lück in the book "Feuchtigkeit, Grundlagen, Messem, Regeln" (Moisture, Fundamentals, Measurement, Control) page 221 and following (Publisher R. Oldenbourg, Munich 1964), the capacitance of a measurement capacitor is determined by the measurement of the voltage on an LC parallel oscillating circuit at a frequency at which the slope of the leading or trailing edges of the oscillating circuit response is maximized. Alternatively the measurement capacitor is inserted into the oscillator as a frequency determining element.

The known moisture measurement arrangements have the disadvantage that the measurements depend upon the absolute value of the voltage applied to the measurement capacitor. The measurement voltage is applied to the measurement capacitor in the form of a direct current voltage or an alternating current voltage of constant frequency. The indicated value of the measured moisture therefore depends directly upon the measurement voltage. However it is problematic whether the measurement voltage applied to the capacitor can be held constant in order to obtain reproducible, reliable results. Therefore the measurement arrangements are relatively imprecise.

The problem to be overcome by the invention is seen as the improvement of the precision of an arrangement for the measurement of the moisture of harvested crop.

BRIEF DESCRIPTION OF THE INVENTION

A feature of the invention includes varying the frequency of the alternating current measurement signal which is applied to the resonance circuit and detecting a parameter of the resonance circuit at various frequencies. Since the frequency dependent parameter of the resonance circuit depends among other things upon the capacitance of the measurement capacitor, the moisture content of the crop to be measured can be determined on the basis of the measured frequency dependent parameter.

By varying the frequency and detecting the frequency dependent parameter, the absolute value of the measured signal no longer represents a source of error, since only the frequency dependency, not the absolute value of the signal, is relevant for the further evaluation. Therefore the measurement device according to the invention operates very precisely.

The parameter of the resonance circuit that is detected most effectively is its impedance. It would also be conceivable to detect the phase shift between a measurement signal that is applied to the oscillating circuit over a high resistance value, and the voltage present at the oscillating circuit as parameter of the resonance circuit. The phase shift is also dependent upon the capacitance of the measurement capacitor and permits a determination of the moisture of the crop to be measured.

For the determination of the impedance of the resonance circuit, a signal is applied to a voltage divider circuit, one arm of which includes the resonance circuit. In one embodiment, the signal is applied to the resonance circuit via resistor or capacitor, and the amplitude of the signal is measured at the resonance circuit. The voltage detected at the resonance circuit depends upon the impedance of the resonance circuit.

The measurement of the impedance of the resonance circuit can be performed in particular in such a way that it is connected through a constant current source with the measurement signal. The constant current source may be, in particular, a constant alternating voltage source that is connected by means of a sufficiently large resistor to the resonance circuit, so that the current through the resonance circuit is constant and is independent of its impedance; then the voltage at the resonance circuit is a direct representation of its impedance. Alternatively a current could also be measured that flows through the resonance circuit. This could employ a shunt resistor on which a voltage is detected that is proportional to the current and is also a representation or measure for the impedance of the resonance circuit. In this case the measurement signal is applied to the resonance circuit through a constant voltage source.

The resonance circuit is preferably a parallel oscillating circuit. In comparison to a series oscillating circuit, which fundamentally could also be utilized, the advantage lies in the fact that the resonant frequency is independent of parasitic resistances connected in parallel that can be caused by surface moisture of the measured crop.

On the basis of the frequency-dependence of the parameter detected, the resonant frequency of the resonance circuit is preferably determined which, for a known and fixed inductance L, is a measure of the capacitance C of the measurement capacitor. The capacitance, in turn, permits a determination of the dielectric constant of the harvested crop contained in the measurement capacitor, which is a function of the moisture of the harvested crop. Hence the moisture can also be determined without difficulty. The resonant frequency is located at that frequency at which the impedance of the resonance circuit is a maximum (parallel oscillating circuit) or a minimum (series oscillating circuit); however other criteria for the determination of the resonant frequency are conceivable, such as the phase shift. In the evaluation of the moisture of the crop by software it is optional whether in the calculation of the moisture intermediate calculation steps are used in which the resonant frequency and/or the capacitance of the capacitor and/or the dielectric constant $\epsilon$ are determined explicitly, or whether the moisture is determined directly on the basis of the measured parameters or on the basis of a frequency, capacitance, dielectric constant or any appropriate value derived in any way from the measured parameters.

Since the temperature at which the measurement is performed as well as the type of the harvested crop have an effect upon the dependence between the dieletric constant and the moisture, the moisture is preferably determined on the basis of a table in which for the ambient temperature, which is detected by means of an appropriate sensor, and/or the actual type of crop (particularly type of grain crop) that can be provided as input by the user, a moisture value is assigned to the measured resonance frequency. Instead of a moisture value that is a function of the resonance frequency, the table can also store the moisture as a function of the capacitance C, the dielectric constant, or any desired other value derived from these values. Such tables can be calibrated by measurements with known parameters.

Furthermore the frequency of the measurement signal which is applied to the resonance circuit can be varied continuously or in steps. A continuous scanning of the frequency range (wobbling) can be generated by analog or digital circuit techniques by means of a triangular or saw tooth-shaped control signal that is applied to a voltage controlled oscillator (VCO). The step-wise scanning of the frequency range can be produced by a step-shaped control voltage of the VCO, which can also be attained by analog or digital switching techniques. A purely digital generation of the measurement signal by means of a digital-analog converter is also conceivable. A preferably pre-determined frequency range is scanned which includes the expected resonant frequency of the resonance circuit. It is also conceivable that several scans be performed of which a first one uses relatively large steps and a second covers only a smaller region in order to cover the resonance retrieved in the first scan, but uses considerably smaller steps, so that the resonant frequency is determined precisely.

Besides the determination of the resonant frequency, the measurement process according to the invention also permits the determination of the width of the resonance curve of the resonance circuit. The wider the response curve, the greater the damping by parasitic resistances that are connected in parallel to the resonance circuit. Parasitic resistances of this kind are usually caused by surface moisture of the crop to be measured that produces an Ohmic resistance between the electrodes of the measurement capacitor. An obvious solution therefore is to evaluate the width of the resonance curve for the sake of the determination of the surface moisture. It does not matter which width of the resonance curve is determined (base width, half value width, etc.). The measured surface moisture can be displayed by means of an indicator arrangement. When a threshold value is exceeded, an error signal can be transmitted, since a value above threshold indicates the crop is obviously too moist to be harvested.

The invention can preferably be applied in agricultural machines, in particular in combines, also known as combine harvesters, or forage harvesters, in which the moisture of the harvested crop (normally grain crops) can be determined. The measured moisture values, as well as surface moisture values, if applicable, can be used for yield mapping and be stored geographically referenced or transmitted by remote data transmission to a central office.

DETAILED DESCRIPTION OF THE PREFERRED EMBODIMENT

Figure 1:
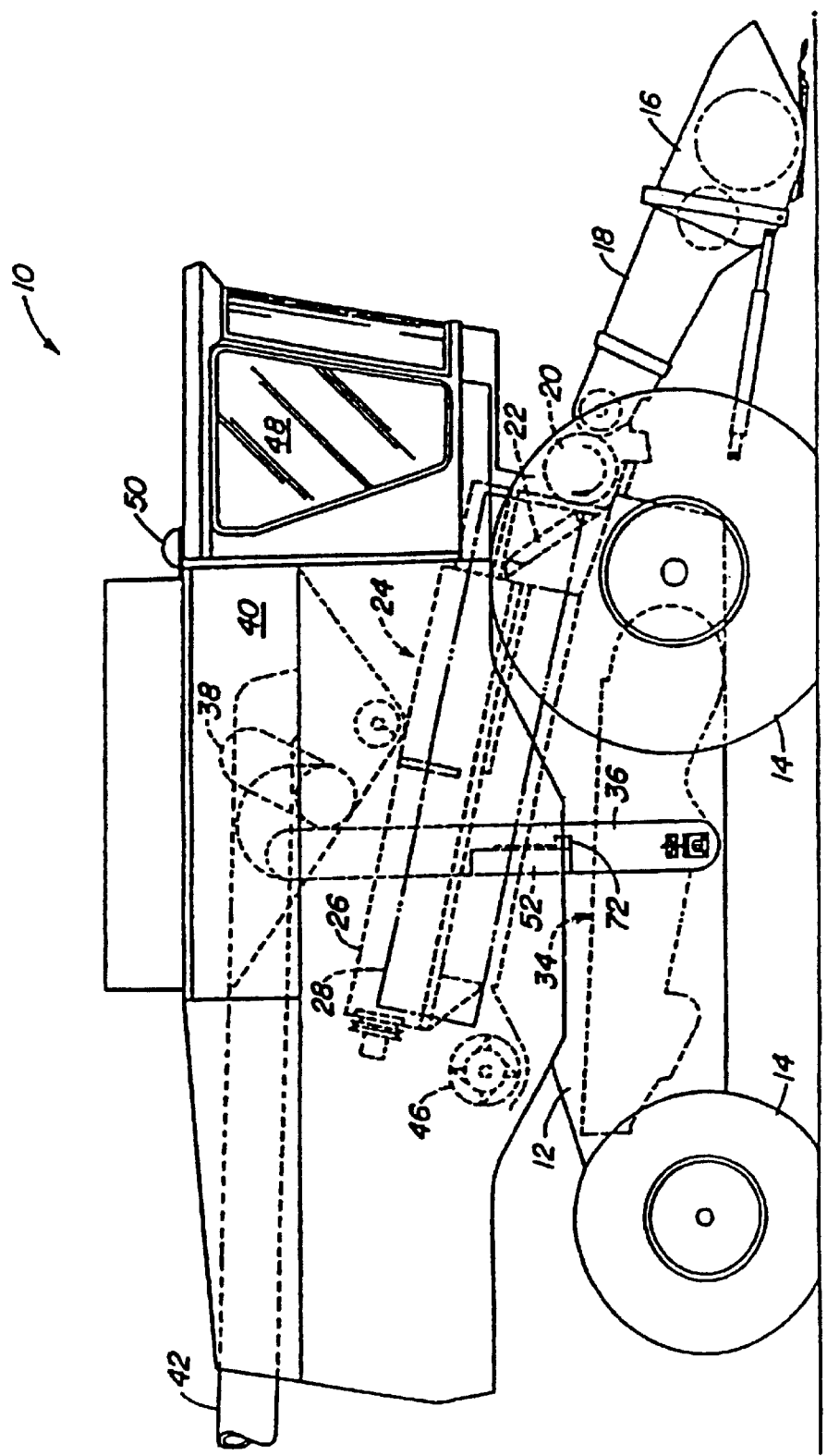
FIG. 1 shows a side view of an agricultural axial flow combine.

FIG. 1 shows an agricultural combine 10 with a chassis 12 and running wheels 14 supporting it on the ground. A header 16 is used to take up crop and to conduct it to a feederhouse 18. The crop is conducted by the feederhouse 18 to a beater 20. The beater 20 guides the crop upward through an intake transition region 22 to a rotary thresher and separator 24. Although the invention is described on the example of a rotary combine, it can also be applied to other combines with an elevator for clean grain such as conventional straw walker machines.

The rotary thresher and separator 24 comprises a rotor housing 26 and a rotor 28 arranged in the rotor housing 26. The harvested crop enters the rotor housing 26 through the intake transition region 22. The rotary thresher and separator 24 threshes and separates the harvested crop. Grain and chaff fall through grates at the bottom of the rotor housing into a cleaning system 34. The cleaning system 34 removes the chaff and conducts the clean grain to a grain elevator 36 which conducts it in turn to a distributing screw conveyor 38. The distributing screw conveyor 38 deposits the clean grain in a grain tank 40. The clean grain in the grain tank 40 can be unloaded through an unloading screw conveyor 42 into a trailer or a truck. Threshed straw separated from the grain is conducted out of the rotary thresher and separator 24 through an outlet to a discharge beater 46. The discharge beater 46 ejects the straw at the rear end of the combine 10.

The operation of the combine 10 is controlled from an operator's cab 48. A receiver 50 for the reception of GPS signals (global positioning system) is attached above the operator's cab 48.

Figure 2:
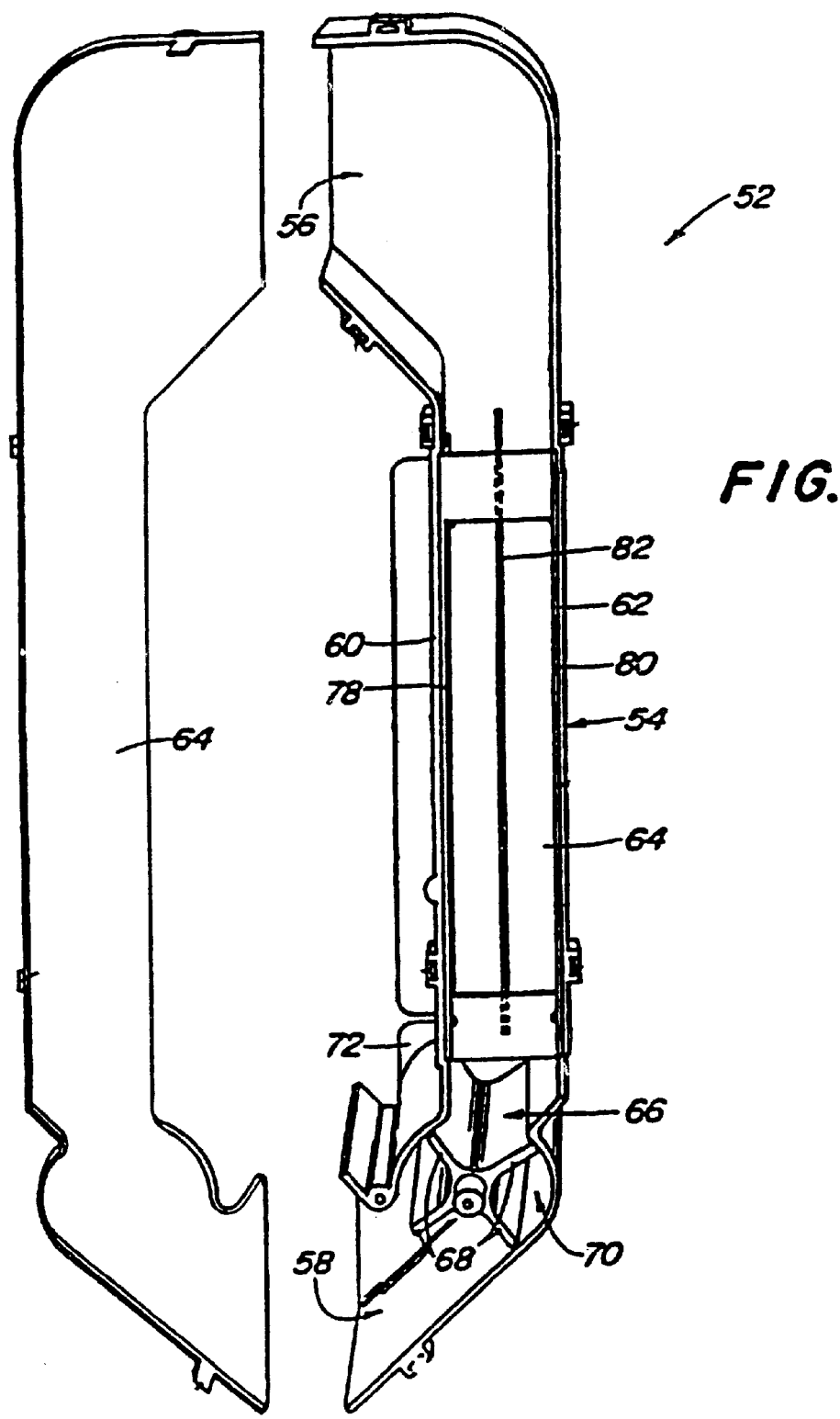
FIG. 2 shows a section through a measurement capacitor of a device for the measurement of the moisture of the harvested crop.

Mounted on one side of the grain elevator 36 is a measurement capacitor 52 of a device for the measurement of the moisture of the grain. The measurement capacitor 52 is shown in greater detail in FIG. 2 and comprises a vertical chamber 54 with an inlet 56 that receives clean grain from the grain elevator 36 and an outlet 58, through which the grain is again returned to the grain elevator 36. The chamber 54 itself has a first wall 60 which is adjacent to the grain elevator 36 and extends parallel to it. A second wall 62 of the chamber 54 extends parallel to the first wall 60 and is spaced at a distance from it. Side walls 64 connect the first wall 60 and the second wall 62. The chamber 54 is made from a non-conducting material such as plastic. One of the side walls 64 is removable and is shown in FIG. 2 in the removed position.

A device for the control of the flow of the grain through the measurement capacitor 52 comprises a paddle wheel 66 that is arranged immediately upstream of the outlet 58. The paddle wheel 66 contains four flexible rubber paddles 68 that extend over the entire width of the chamber 54 between the side walls 64. A cylindrical region 70 is formed in the chamber 54 to accept the paddle wheel 66. The paddle wheel 66 is driven by an electric motor 72. The paddle wheel 66 is operated to control the flow of grain through the chamber 54 in such a way that an amount of grain adequate for a measurement of the moisture is contained therein. A corresponding control is disclosed in CA 2182989 A, incorporated herein by reference.

The chamber is also equipped with electrodes for the measurement of capacitance that include first, second and third metal plates 78, 80 and 82. The first two metal plates 78, 80 are located next to each other, are parallel to the first and second walls 60, 62 and are connected electrically to each other. The third metal plate 82 extends parallel to the first two metal plates 78, 80 and is arranged centrally between them. Clean grain flowing between the metal plates 78, 80, 82 is a dielectric material that has an effect on the capacitance between them that is a function of the moisture of the material.

Figure 3:
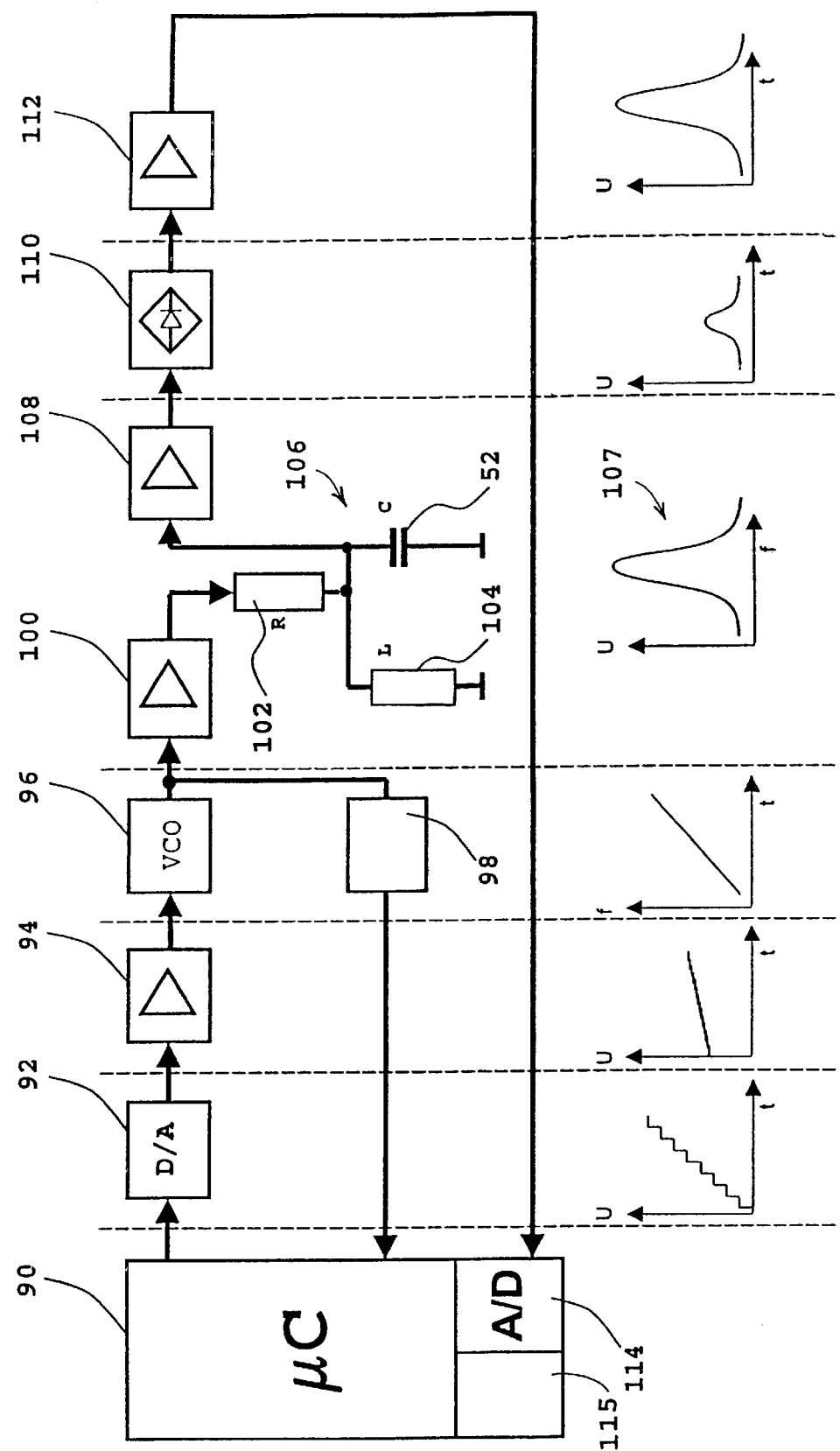
FIG. 3 shows a circuit diagram of the device for the measurement of the moisture.

FIG. 3 shows a block circuit diagram of a device for the determination of the moisture of the grain. It comprises a micro-controller 90 (a microprocessor could also be used in place of the micro-controller) and a digital-analog converter 92 that is controlled by the micro-controller 90 and whose output signal is conducted to a compliance amplifier 94. The amplifier 94 assures that the magnitude of the output voltage of the digital-analog converter 92 is converted to the proper range for controlling a voltage controlled oscillator (VCO) 96. The output of the voltage controlled oscillator 96 is connected to the input of a second amplifier 100 and to the input of a frequency counter 98.

The micro-controller 90 transmits a (digital) signal to the digital-analog converter 92 that causes the latter to deliver a step-shaped voltage at its output. The variation of voltage with time at the output of the digital-analog converter 92 is reproduced in FIG. 3 under the digital-analog converter 92. The compliance amplifier 94 delivers an output voltage reproduced under it in FIG. 3 which has a flatter shape and which has the effect of causing the voltage controlled oscillator 96 to provide a range of frequencies sufficiently covering the resonance region of a resonance circuit 106 in which the capacitor 52 is located. At the output of the voltage controlled oscillator 96 a sine-wave shaped alternating voltage is available, whose frequency increase with time in a saw-tooth shaped pattern. This so-called wobble signal is reproduced in FIG. 3 under the voltage controlled oscillator 96.

The frequency counter 98 delivers in turn to the micro-controller 90 a digital signal that contains information about the actual frequency. While it would be conceivable to determine a nominal value of the frequency on the basis of the signal supplied by the micro-controller 90 to the digital-analog converter 92, such determination would be relatively imprecise because of the temperature dependence of the voltage-frequency characteristic of the voltage controlled oscillator 96. By determining the immediate frequency by means of the frequency counter 98, the micro-controller 90 can be supplied with a more precise, temperature-independent value of the frequency.

The amplifier 100 which, as a rule, is a voltage follower, amplifies the output signal of the voltage controlled oscillator 96 and transmits the amplified signal to a resistor 102 having a more or less high Ohmic resistance. Alternatively, a capacitor with lower capacitance could be employed. The amplifier 100 and the resistor 102 define together with the resonance circuit 106, which is composed of an inductance 104 and the capacitor 52, a voltage divider. The signal developed at the "hot" or input end of the resonance circuit 106 is a function of the impedance of the resonance circuit 106. If the value of the resistor 102 is selected sufficiently high, it acts essentially as a current source. The output current is substantially constant, that is, independent of the frequency and the impedance of the resonance circuit 106. The value of the voltage at the resonance circuit 106 is then directly proportional to its impedance.

The connection to the resistor 102 opposite its connection with the amplifier 100 is connected to the parallel resonance circuit 106. The capacitor 52 in the resonance circuit 106 consists of the metal plates 78, 80, 82 of which the third metal plate 82 is connected with the resistor 102 and the first two metal plates 78, 80 are at mass potential or ground (or vice versa). A frequency-dependent voltage is provided at the "hot" end of the resonance circuit 106, that is, at the connection to the resistor 102 with the circuit 106 the amplitude $U_o$. This frequency-dependent voltage, the amplitude of which is shown in the resonance curve 107 in FIG. 3 under the resonance circuit 106, is a measure of the impedance of the resonance circuit 106, and peaks at the resonant frequency. It is well known that the resonant frequency lies in the vicinity of $\frac{1}{2}\pi(LC)^{1/2}$. Due to the linear dependence of the frequency on time (see the curve under the voltage controlled oscillator 96), the amplitude could be plotted as a function of the time instead of a function of the frequency, without a change in the shape of the curve.

In embodiments of the invention, the amplification factor of the amplifier 100 may be controlled by the micro-controller 90. This arrangement permits the voltage amplitude applied to the resonance circuit 106 to be adjusted. For example, when a strong damping is caused by parasitic resistances that result from surface moisture of the crop, the amplitude of the output of the amplifier 100 can be increased accordingly to obtain a sufficient input signal at a third amplifier 108.

The voltage applied to the resonance circuit 106 is amplified by means of the third amplifier 108 (which is preferably a voltage follower) and is transmitted to a rectifier 110, which rectifies the signal. The rectified signal is again amplified by a fourth amplifier 112, which preferably is a voltage follower. At the output of the rectifier 110, a time-dependent (direct current) voltage is provided that is proportional to the amplitude of the voltage present at the resonance circuit. This time-dependent voltage, illustrated in FIG. 3 below the rectifier 110, is amplified by the fourth amplifier 112. The output signal from the fourth amplifier 112, illustrated under it in FIG. 4, is applied to the input of a digital-analog converter 114 integrated into the micro-controller 90.

The micro-controller 90 is controlled by software that is stored in a RAM or ROM. A measurement of the moisture of the harvested grain can be performed continually or upon an input from the operator of the combine. For the measurement of the moisture the micro-controller 90 scans a frequency range around the resonant frequency of the resonance circuit 106 and determines the resonant frequency on the basis of the output value of the digital-analog converter 114 Since the capacitance of the capacitor 52 via dielectric constant depends upon the moisture of the grain, and, in turn, the resonant frequency of the resonance circuit 106 depends upon the capacitance, a simple but precise measurement of the moisture of the grain is possible. The moisture is determined on the basis of the measured resonant frequency with the use of a table or other stored mathematical relationships in a memory device 115. The moisture values thus determined can be used with the application of the positional signals of the GPS receiver 50, stored in memory with a geographical reference using the positional signals of the GPS receiver 50 or used in other ways.

Figure 4:
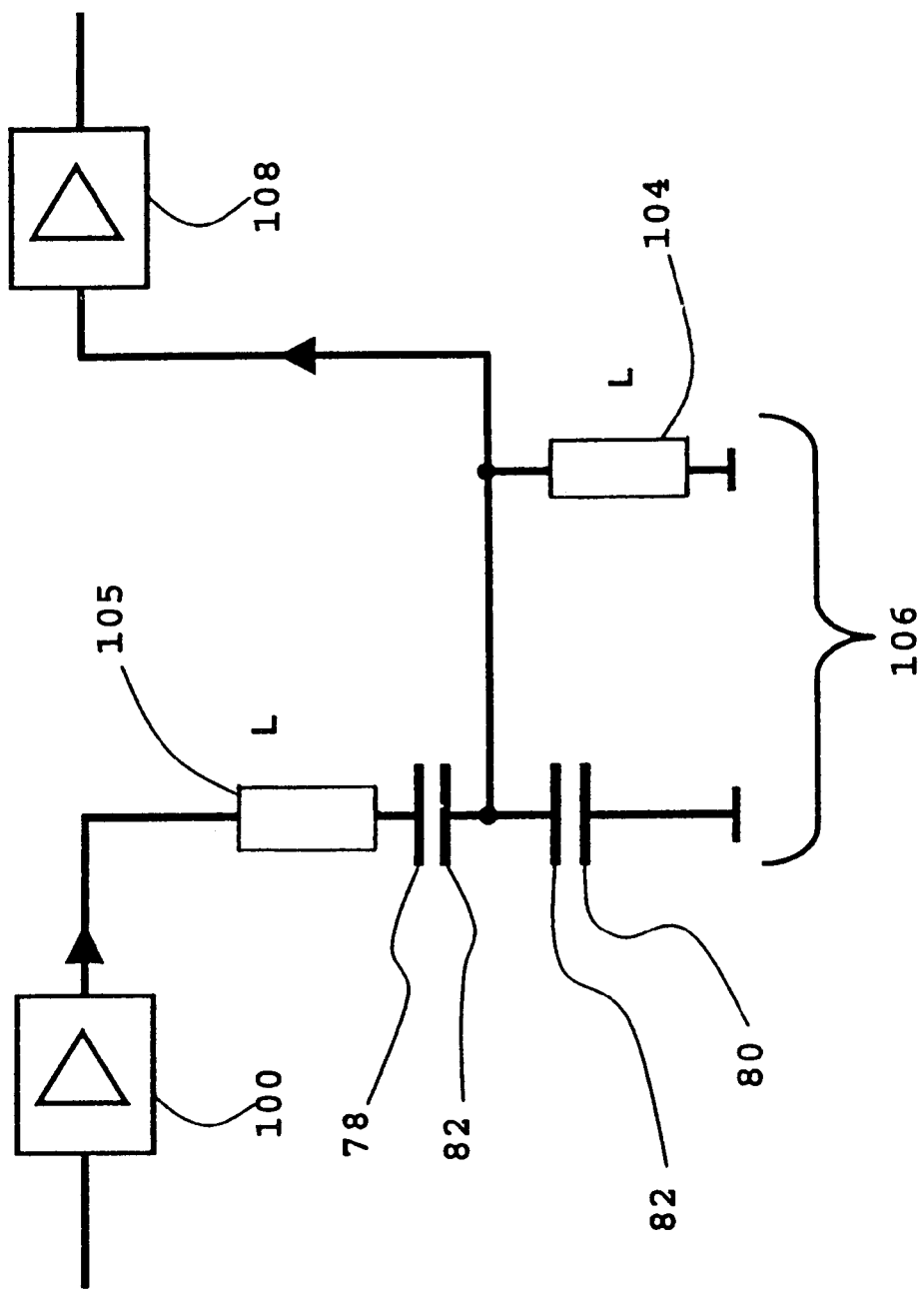
FIG. 4 shows a section of FIG. 3 with an alternative voltage divider circuit.

FIG. 4 shows a modified circuit arrangement of the voltage divider of FIG. 3, in which only the pair of metal plates 80, 82 is used in the resonance circuit 106. The inductance 104 is connected in parallel with this pair of plates 80, 82. The signal at the plates is applied to the amplifier 108. The output of the amplifier 100 is connected to the first lead of a second inductor 105 having an inductance which preferably coincides with that of the inductance 104. The second lead of the inductor 105 is connected to the remaining metal plate 78. A voltage divider is thereby defined including a series resonance circuit (the second inductor 105 and the pair of metal plates 78, 82) and a parallel resonance circuit (circuit 106 including the inductor 104 and the pair of metal plates 80, 82). The frequency-dependent signal is provided at the central metal plate 82. This voltage divider circuit has a response curve with steeper slopes than that shown in FIG. 3, and therefore permits a better recognition of the resonant frequency. Obviously the connections of the metal plates 78, 80 can be interchanged.

Having described the preferred embodiment, it will become apparent that various modifications can be made without departing from the scope of the invention as set forth in the accompanying claims.

We claim:

1. Device for the measurement of the moisture of harvested crop, including a resonance circuit comprising a measurement capacitor having two spaced electrodes, an output, and an inductance connected to the capacitor to define a resonance circuit parameter dependent on moisture content of material between the electrodes, a source of variable frequency alternating voltage connected to the resonance circuit, and a detector connected to the output of the resonance circuit and responsive to the variable frequency alternating voltage for detecting the parameter of the resonance circuit at various frequencies, the device further including structure introducing harvested crop between the electrodes to vary the parameter, the detector providing an indication of the moisture of the harvested crop from the detected parameter.

2. The device as set forth in claim 1 wherein the detected parameter is a function of the impedance of the resonance circuit.

3. The device as set forth in claim 2 including a voltage divider, wherein the resonance circuit comprises a part of the voltage divider, and wherein the variable frequency alternating voltage measurement signal is supplied to the voltage divider and the detector is responsive to the voltage at the output of the resonance circuit.

4. The device as set forth in claim 3 wherein the divider includes a high impedance device connected to the source of alternating voltage to define a constant current source.

5. The device as set forth in claim 2 wherein the measurement signal is supplied to the resonance circuit as a constant voltage source, and wherein the current level through the resonance circuit is detected.

6. The device as set forth in claim 1 wherein the source of variable frequency alternating voltage comprises a controlled oscillator providing a frequency signal continuously varied over a range of frequencies including the resonant frequency of the resonance circuit.

7. The device as set forth in claim 1 wherein the source of variable frequency alternating voltage comprises a variable frequency oscillator having an output signal varied in steps over a predetermined frequency range including the resonant frequency of the resonance circuit.

8. The device as set forth in claim 1 wherein the resonant circuit defines a resonance curve having a width dependent on surface moisture of the crop to be measured, and wherein the detector detects the width of the resonance curve of the resonance circuit to provide an indication of the surface moisture.

9. The device as set forth in claim 8 including an indication device responsive to the indication of surface moisture and providing an error message when the surface moisture exceeds a threshold value.

10. The device as set forth in claim 1 including a harvested crop receivingcontainer mounted on an agricultural machine, the container housing the measurement capacitor.

11. The device as set forth in claim 10 including a device directing harvested crop through the measurement container.

12. Device for the measurement of the moisture of harvested crop, including a resonance circuit comprising a measurement capacitor having two spaced electrodes and an inductance connected to the capacitor to define a resonance circuit parameter dependent on moisture content of material between the electrodes, a source of variable frequency alternating voltage connected to the resonance circuit and a detector circuit connected to the resonance circuit and responsive to the variable frequency alternating voltage for detecting the parameter of the resonance circuit at various frequencies, the device further including structure introducing harvested crop between the electrodes to vary the parameter, the detector circuit providing an indication of the moisture of the harvested crop from the detected parameter, and wherein the resonance circuit is a parallel resonance circuit.

13. The device as set forth in claim 12 wherein the parameter is resonance frequency, the detector circuit including a memory device storing moisture values that are functions of the resonant frequency of the resonance circuit.

14. The device as set forth in claim 13 wherein the moisture values are functions of temperature and type of the harvested crop.

15. Device for the measurement of the moisture of harvested crop, including a resonance circuit comprising a measurement capacitor having two spaced electrodes and an inductance connected to the capacitor to define a resonance circuit parameter dependent on moisture content of material between the electrodes, a source of variable frequency alternating voltage connected to the resonance circuit and a detector circuit connected to the resonance circuit and responsive to the variable frequency alternating voltage for detecting the parameter of the resonance circuit at various frequencies, the device further including structure introducing harvested crop between the electrodes to vary the parameter, the detector circuit providing an indication of the moisture of the harvested crop from the detected parameter and including a processor, wherein the resonance circuit has a resonant frequency and the processor includes a memory device storing moisture values that are functions of the resonant frequency of the resonance circuit, and wherein parameters of the resonance circuit detected at different frequencies are processed by the processor for calculating the resonant frequency.

16. Process for the measurement of moisture of harvested crop, including the following steps:

providing a resonance circuit having an inductor and a measurement capacitor with two electrodes;

introducing harvested crop between the two electrodes;

supplying a signal to the resonance circuit in the form of an alternating voltage of variable frequency;

varying the frequency of the signal supplied to the resonance circuit;

determining a frequency-related parameter of the resonance circuit based on the response of the resonance circuit to varying of the frequency of the signal; and determining moisture on the basis of the determined frequency-related parameter.

17. The process as set forth in claim 16 wherein the step of varying the frequency of the supplied signal includes varying the frequency over a range of frequencies which includes the resonant frequency of the resonance circuit, and the step of determining moisture includes determining the capacitance of the measurement capacitor.

18. The process as set forth in claim 16 wherein the step of determining moisture includes determining the resonant frequency of the resonance circuit with the harvested crop between the two electrodes.

19. The process as set forth in claim 16 wherein the step of introducing harvested crop includes introducing a flow of crop between the two electrodes.

20. The process as set forth in claim 18 wherein the step determining moisture includes determining the resonance response curve of the resonance circuit.

21. The process as set forth in claim 16 including providing an indication of surface moisture of the crop utilizing a parasitic resistance of the resonance circuit.

* * * * *